(12) United States Patent
Hall

(10) Patent No.: US 7,739,127 B1
(45) Date of Patent: Jun. 15, 2010

(54) AUTOMATED SYSTEM FOR FILING PRESCRIPTION DRUG CLAIMS

(76) Inventor: Stephen Don Hall, 6265 Country Vale La., Pinson, AL (US) 35126

(*) Notice: Subject to any disclaimer, the term of this patent is extended or adjusted under 35 U.S.C. 154(b) by 1665 days.

(21) Appl. No.: 10/948,779

(22) Filed: Sep. 23, 2004

(51) Int. Cl.
*G06Q 10/00* (2006.01)
*G06Q 50/00* (2006.01)

(52) U.S. Cl. .......................................................... 705/2
(58) Field of Classification Search ...................... 705/2, 705/4
See application file for complete search history.

(56) References Cited

U.S. PATENT DOCUMENTS

| | | | |
|---|---|---|---|
| 4,491,725 A * | 1/1985 | Pritchard | 705/2 |
| 4,858,121 A | 8/1989 | Barber | |
| 4,916,611 A | 4/1990 | Doyle, Jr. | |
| 5,070,452 A | 12/1991 | Doyle, Jr. | |
| 5,301,105 A | 4/1994 | Cummings, Jr. | |
| 6,012,035 A | 1/2000 | Freeman, Jr. | |
| 6,208,973 B1 | 3/2001 | Boyer | |
| 6,873,960 B1 * | 3/2005 | Wood et al. | 705/4 |
| 2002/0002495 A1 | 1/2002 | Ullman | |
| 2002/0138309 A1 | 9/2002 | Thomas, Jr. | |
| 2002/0198831 A1 | 12/2002 | Putricelli | |
| 2003/0018495 A1 | 1/2003 | Sussman | |
| 2003/0055687 A1 | 3/2003 | Rudy | |
| 2003/0195773 A1 | 10/2003 | Mahaffey | |
| 2004/0103061 A1 | 5/2004 | Wood | |
| 2004/0103062 A1 | 5/2004 | Wood | |

* cited by examiner

*Primary Examiner*—Gerald J. O'Connor
*Assistant Examiner*—John A Pauls

(57) ABSTRACT

An automated system and method for filing prescription drug claims which includes a point of service terminal which accepts a payment system access card for payment for a purchase of a service and/or product by a customer, where at least part of the purchase is reimbursable by a third party payor. The point of service terminal creates a purchase transaction and during the transaction electronically captures pertinent claim information including a claim authorization or approval number. The point of service terminal uses the pertinent claim information to update a claim records database. The claim records database is accessed by the third party payor and the pertinent claim information is validated. The applicable reimbursement amount, which is determined by the third party payor, is issued as a credit to the customer payment card account or a customer bank account or as a check.

9 Claims, 3 Drawing Sheets

100
Issue cobranded healthcard/payment card to insurance subscriber

102
Insurance subscriber uses payment card to purchase a prescription for which a claim authorization number has been issued

104
Point of service equipment electronically captures pertinent claim information including the claim authorization number and uses the information to create or update a claim records database

106
Third party payor accesses claim records database and validates claim records

108
Third party payor reimburses insurance subscriber for applicable reimbursement amount

Fig. 2

AUTOMATED SYSTEM FOR FILING PRESCRIPTION DRUG CLAIMS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

This invention relates generally to a health insurance indemnity system in which insurance subscribers are required to make payments to service providers and then claim and collect from insurers and more specifically to an automated system and method by which an insurance company or third party payor could allow subscribers to file prescription drug claims.

Many health insurance companies and medical plans offer what is sometimes referred to as a major medical point-of-service prescription drug benefit plan. In this benefit plan, customers or insurance subscribers are responsible for paying for their prescription drugs in full. The insurance subscribers are then required to file prescription drug claims for reimbursement of a specified portion of these expenses. Typically the reimbursement amount ranges from 50% to 100% depending on the type of medication and whether or not the subscribers have reached their maximum "out of pocket" limits. The reimbursement portion can represent a significant amount of money to subscribers who have high prescription drug expenses and low or fixed incomes. Loss or misplacement of even one or two prescription receipts could result in a significant loss of money for these insurance subscribers, if they fail to file a claim for reimbursement. Information needed for filing a claim is readily available from their pharmacist should a receipt be lost, but not everyone is aware of this. It can be difficult to document and track which prescriptions have had claims filed and which ones have not. In order to track this effectively, one would need to keep a log of every prescription purchase. It would also be necessary to keep a spreadsheet to document that a claim was filed for each prescription and that the reimbursement check was received and deposited. This can be overwhelming for people who have no accounting background and unnecessarily expensive for those who have problems with memory loss. There is a need in the art to automate the filing of prescription drug claims for insurance subscribers, even though there have been significant advances in the art with regards to automating the filing and collection of insurance claims on behalf of service providers.

Boyer, in U.S. Pat. No. 6,208,973 B1 describes a Point of Service Third Party Financial Management Vehicle for the Healthcare Industry that comprises the steps of: "transmitting at least one of healthcare product and service codes for healthcare products and services purchased by the patient from a healthcare provider at a point of service to an adjudication engine for processing; The adjudication engine adjudicating the product and service codes substantially in real-time so as to determine a first portion of the purchased healthcare products and services which is to be paid by a third party payor and a second portion of the purchased healthcare services which is to be paid by the patient; the adjudication engine returning an adjudicated settlement transaction to the point of service designating at least the first portion and the second portion; formatting the adjudicated settlement transaction as a credit card transaction at the point of service; and processing the formatted adjudicated settlement transaction in a credit card network for payment". The present invention makes no attempt to include an adjudication engine as part of the invention. It does not use a product or service code as information to be used in an adjudication process, but rather uses a claim authorization or approval number that an insurance company or third party payor issues to a pharmacist. The third party payor determines an applicable reimbursement amount and that adjudication process is not within the scope of this invention. Boyer's invention does not address needs of insurance subscribers where their insurance company or third party payor does not subscribe to his Point of Service Third Party Financial Vehicle.

Richard O Ullman in Patent Application Pub. No.: US 2002/0002495 A1 describes an invention that relates generally to the field of consumer prescription and other healthcare programs and more particularly to an integrated consumer rewards program for prescription medication users. A participating consumer with one card, can instantly purchase pharmaceuticals and charge the transaction to a credit card and earn and apply savings dollars redeemable for pharmaceutical purchases. The invention claims a system for managing pharmaceutical accounts comprising: a plurality of points of sale, said points of sale adapted for transacting pharmaceutical sales with consumers; a processor coupled to said plurality of points of sale, said processor adapted to adjudicate claims associated with said pharmaceutical sales; and a financial processor coupled to said processor for processing any electronic financial transactions associated with said pharmaceutical sales; whereby a percentage of said pharmaceutical sales is credited to a rewards account for said consumers. Again, the present invention does not use a processor adapted to adjudicate claims and does not include a rewards program. Ullman's invention does not address the needs of insurance subscribers where their insurance company or third party payor uses its own adjudication process for determining the applicable reimbursement amount and requires subscribers to file claims for reimbursement.

Robert G. Mahaffey, in Patent Application Pub. No.: US 2003/0195773 A1 describes a method for payment of healthcare charges by paying the amount due with a healthcare credit card and the patient receiving a first discount from the amount due. The credit card issuing company pays the healthcare provider an amount equal to the patient charge less the first and less a second discount. The healthcare provider minimizes its accounts receivable, the patient receives a discount from the amount due and the charge card issuer earns a profit due to a payment to the healthcare provider of a double discounted amount while collecting from the patient a single discount amount. The present invention does not use the discounting scheme described in this patent application. Mahaffey's invention does not address the needs of insurance subscribers where their insurance company or third party payor uses its own adjudication process for determining the applicable reimbursement amount and requires subscribers to file claims for reimbursement.

The above mentioned patents describe the use of payment cards to automate the adjudication of claims and the securing of rewards or discounts, but they do not address the specific situation that the present invention addresses. That situation is that under some prescription drug programs it is necessary for the program subscribers to pay for their prescriptions in full "out of pocket" and then file prescription drug claims for reimbursement. If subscribers fail to file claims, the subscribers lose the reimbursement amount that they are due according to terms of their insurance contract. The present invention addresses this problem.

Furthermore, prescription drug insurance companies must pay employees to manually process their prescription drug paper claims. If employed, the present invention should considerably reduce expenses associated with processing paper claims. The present invention has been designed to meet the need in the art to automate the filing of subscriber prescription drug claims where a claim authorization or approval number has been issued by the third party payor prior to a sale.

BRIEF SUMMARY OF THE INVENTION

The present invention addresses the above mentioned needs in the art by providing a system by which a customer or insurance subscriber can automatically file a prescription drug claim simply by using a particular payment card that has been linked to his or her insurance contract. In accordance with the invention, such a system comprises a point of service terminal which accepts a payment system access card such as a credit card, debit card, or purchase card, for payment for a purchase of a service and/or product by a customer, where at least part of the purchase is reimbursable by a third party payor. In a preferred embodiment of the invention, a claim authorization number, which is issued by the third party payor to the pharmacist prior to the sale, is included in a bar code label for the prescription drug. The applicable reimbursement amount is determined by the third party payor when the claim authorization number is issued to the pharmacist. In accordance with the invention, the point of service terminal creates a purchase transaction for the full amount of the purchase. The payment system access card provides access to a payment system which transfers funds as with typical payment card transactions. In addition to creating a purchase transaction, the point of service terminal also updates a claim records database thereby causing said database to contain the claim authorization number needed for filing a prescription drug claim. This updated claim records database is accessible to the third party payor. The third party payor accesses the updated claim records database and validates pertinent claim information. The third party payor then reimburses the insurance subscriber for the applicable reimbursement amount. This reimbursement could occur in real time by issuing a credit to the insurance subscriber's credit card account or bank account. It could also occur during batch processing and by issuing a check to the insurance subscriber.

Objects and advantages of the invention include that it eliminates tedious effort required by customers or insurance subscribers to collect pertinent prescription claim information, to complete and mail prescription drug claims, and to track which prescription claims have been filed and which have not. The present invention, if fully implemented, practically eliminates a potential of failing to file a prescription drug claim and thereby losing a reimbursement amount that the insurance subscriber is rightfully due. This aspect of the invention could result in significant monetary savings to insurance subscribers. Consequently, the invention could lower stress associated with what can be a major expense and burden for insurance subscribers with health problems. The present invention includes a potential of receiving the applicable reimbursement amount in real time at the time of purchase as a credit to an insurance subscriber's payment card account or bank account.

Other objects and advantages are for the third party payor, the insurance company providing the prescription drug benefit plan. There is a significant expense associated with paying employees for opening prescription drug claim mail, microfilming, keying, and otherwise processing paper generated prescription drug claims. Furthermore, there are additional expenses associated with cutting checks and mailing these checks to insurance subscribers. The present invention would dramatically reduce these expenses. Further objects and advantages of the invention will become apparent from a consideration of drawings and their ensuing descriptions.

BRIEF DESCRIPTION OF THE SEVERAL VIEWS OF THE DRAWING

The foregoing and other novel features and advantages of the present invention will become more apparent and more readily appreciated by those skilled in the art after consideration of the following descriptions in conjunction with their associated drawings, of which:

FIG. 2 illustrates a flow diagram of a use of the automated system for filing prescription drug claims.

DETAILED DESCRIPTION OF THE INVENTION

Figure 1:
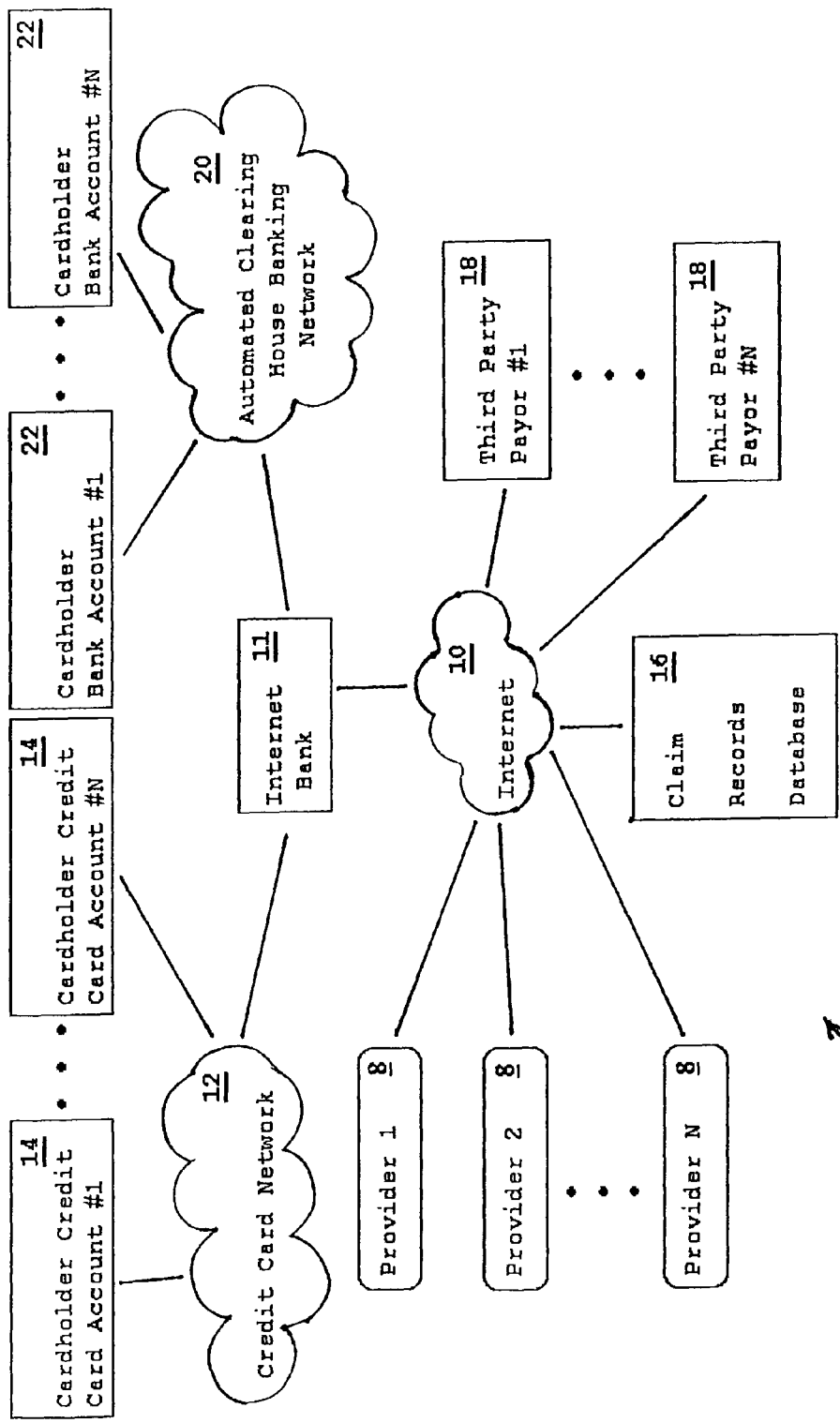
FIG. 1 illustrates an automated system for filing prescription drug claims in accordance with a currently preferred embodiment of the invention.

A preferred embodiment of the present invention will now be described in detail with reference to FIG. 1. Those skilled in the art will appreciate that the description given herein with respect to each figure is for exemplary purposes only and is not intended in any way to limit the scope of the invention. All questions regarding the scope of the invention may be resolved by referring to the appended claims.

Many health insurance companies and medical plans offer what is sometimes referred to as a major medical point-of-service prescription drug benefit plan. In this benefit plan, customers or insurance subscribers are responsible for paying for their prescription drugs in full. The insurance subscribers are then required to file prescription drug claims for reimbursement of a specified portion of these expenses.

The term "claim authorization number" or simply "authorization number" as used herein refers to a number issued to a service provider or pharmacist for a particular prescription, service, or product for a particular insurance subscriber prior to an actual sale of the product or service to the subscriber. At the time the authorization number is issued for a particular prescription, the amount to be charged for the prescription has usually been determined by prior agreement between the pharmacist and the insurance company providing the prescription drug benefit plan. The insurance company or third party payor also normally determines an applicable reimbursement amount at the time the authorization number is issued to the pharmacist. The amount of reimbursement typically ranges from 50% to 100% depending on the type of medication and whether or not the subscriber has reached his or her maximum "out of pocket" limits. Therefore, prior to a prescription drug sales transaction, an insurance company or third party payor database not only contains information such as a subscriber contract number and payment system access card number, but also contains pertinent claim information for subscriber prescriptions such as claim authorization numbers, amounts to be charged for prescriptions, and amounts to be reimbursed to a subscriber should claims be filed. Furthermore, the pharmacy updates its own database with the authorization number and amount to be charged for a particular prescription at the time the authorization number is received. Typically, the required communication between the pharmacy and insurance company to request and receive an authorization number is over the Internet, but may include a phone call if there are issues to be resolved.

The present invention is designed to automate the filing of claims where an authorization or approval number has been issued by the third party payor prior to the sales transaction. FIG. 1 illustrates an automated system 6 for filing claims in accordance with a currently preferred embodiment of the invention. Although described in the preferred context of the filing of prescription drug claims by insurance subscribers, those skilled in the art will appreciate that the system and method of the invention may be used in all types of transactions involving two or more parties obligated contractually or otherwise where one party is obligated to reimburse the other party for a portion of an expense and where an approval number is issued prior to the purchase transaction.

As will be more apparent from the following detailed description, the invention provides a method for automatically filing claims substantially in real-time by providing immediate access by the third party payor to a claim records database. While it is desired that validation and reimbursement take place virtually instantaneously so that reimbursement may be completely settled at the point of service at the time of service, "real-time" as used herein is also intended to permit "batch" processing and settlement of the claims by the third party payor. For example, an insurance company may not determine the applicable reimbursement amount at the time the approval number is issued, but may determine that amount later and then settle all of its claims for a given day overnight by batch processing the claims received that day. In such a case, the claims submitted that day may not actually be paid for a day or two. Similar techniques are used by hotels and airlines and are contemplated within the scope of the invention.

Figure 3:
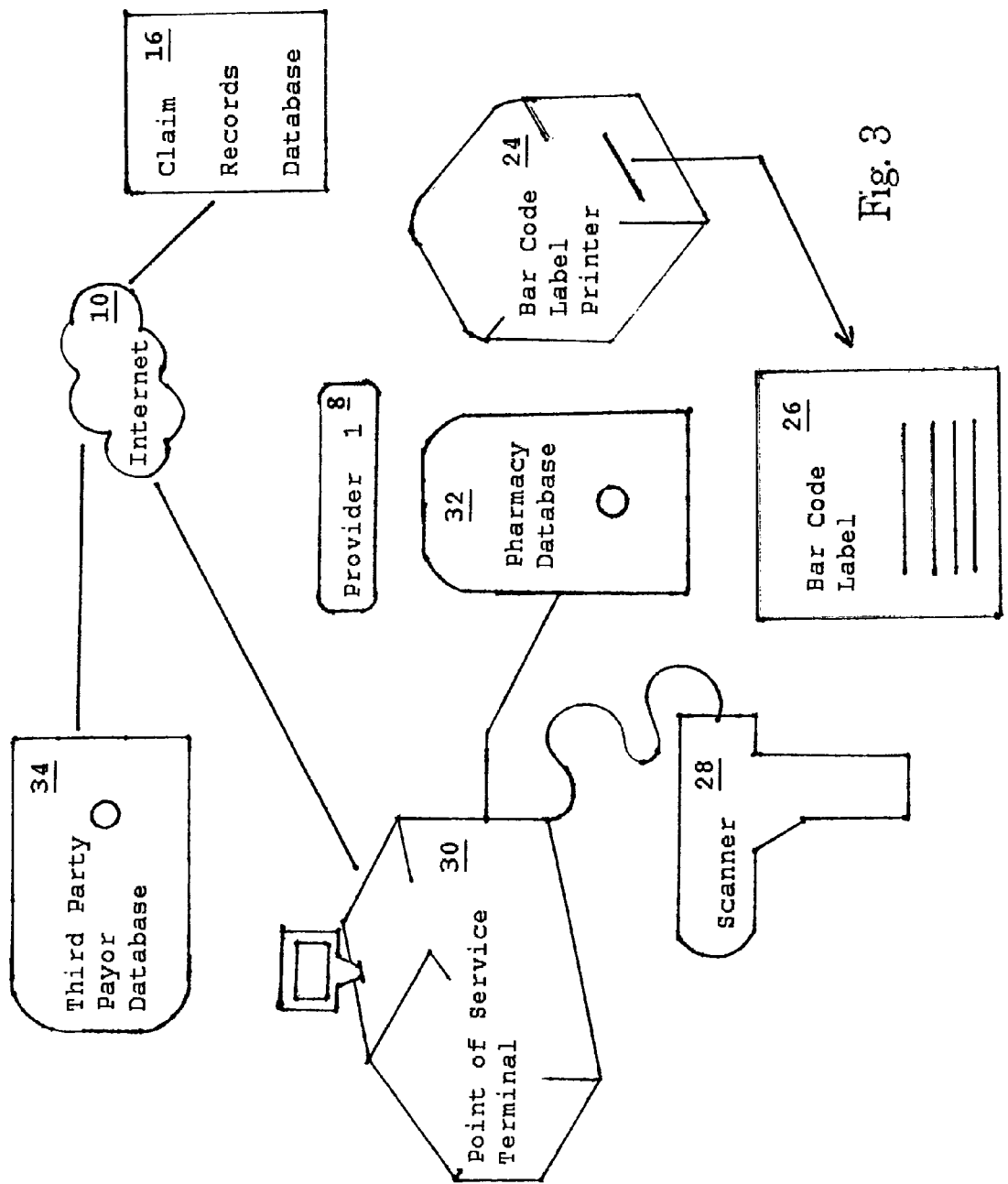
FIG. 3 illustrates uses of a bar code label, a service provider database, and a third party payor database as purchase transaction input data and as input data in updating a claim records database.

As illustrated in FIG. 1, the system 6 of the invention is accessed by a plurality of product/service providers 8, such as doctor's offices, hospitals, pharmacies, and the like, who provide services and products such as physician care, hospital care, dental care, pharmaceutical products, lab tests, prosthetics, surgical equipment, and the like. As illustrated in FIG. 3, in accordance with the invention, each such provider 8 has a point of service terminal 30 which accepts a payment system access card, such as a credit card, debit card, or purchase card, for payment for a purchase of a service and/or product by a customer. As will be explained below, each subscriber has access to an account which is tied to a cardholder, which may be the subscriber or a member of his or her family.

The payment system access card in accordance with the preferred healthcare embodiment of the invention is preferably a cobranded Citibank® card, although other types of payment cards may, of course, be used and cobranding is not required. The "cobranding" partner in such an embodiment is the third party payor, which may include, by way of example, insurance companies, HCFA (Medicare), State Agencies (Medicaid), and self insured groups (HMOs). Typically, the third party payor contracts with the subscriber or the subscriber's employer or some other organization or association to which the subscriber belongs to provide payment through an administrator for services rendered by the healthcare provider. The third party payor also contracts with groups of Healthcare Provider Networks (HCPs) to fix prices on a per subscriber or per procedure basis. Preferably, the cobranded payment system access card is distributed to the insured through the insured's employer in place of the conventional healthcare ID cards. The cobranded card typically includes the information provided on the payment system access card as well as the healthcare ID card, although the amount of printed data may require that some of the information be printed on a sleeve of the payment system access card. The third party payor has a field in each subscriber record for the payment system access card number and therefore an insurance contract number for the subscriber is linked to or associated with the subscriber payment system access card number. The automated claim filing system is accessed by swiping the payment system access card or entering the card number at a point of service terminal 30 in the offices of the healthcare provider 8.

As also illustrated in FIG. 3, each provider 8 has a bar code label printer 24 capable of printing bar code labels 26 that incorporate the claim authorization number as part of the label 26. The bar code label scanner 28 is connected to the provider's point of service terminal 30 in a conventional manner. The provider's point of service terminal 30 includes an Internet connection 10.

As illustrated in FIG. 1, the provider's point of service terminal 30 includes an Internet connection 10 to a node containing an Internet bank 11 which is to process credit card transactions via a credit card network 12 in a conventional manner. The Internet bank 11 operates as a conventional merchant bank for credit card processing by providing access to a credit card network 12 for processing of credit card transactions and also operates as a credit card issuing bank by providing cardholder accounts 14 used to facilitate credit card payment by the cardholder, keep track of balances and interest, and the like.

As illustrated in FIG. 3, in accordance with the preferred healthcare embodiment of the invention, the point of service terminal 30 also includes an Internet connection 10 to a relational claim records database 16. The claim records database stores pertinent claim information that is captured by the provider's point of service terminal 30 during the sales transaction and has fields such as a prescription or Rx#, a date filled or purchased, an amount charged, the payment system access card number, and the claim authorization number. Although referred to as a claim "records" database, the database could consist of only one record.

As illustrated in FIGS. 1 & 3, the claim records database 16 is also accessible to the third party payor 18 through an Internet connection 10. The third party payor 18 maintains a third party payor database 34. The third party payor 18 has an Internet connection 10 to the node containing the Internet bank 11, which is to process credit card transactions such as crediting the cardholder account 14 via the credit card network 12 in a conventional manner. The Internet bank 11 is also capable of processing electronic funds transfers through the automated clearinghouse banking network 20 to the cardholder bank account 22, should the subscriber prefer that method of reimbursement.

In the preferred implementation of the invention, prior to the prescription drug sales transaction, the insurance company or third party payor issues a claim authorization number or approval number to the provider or pharmacy for a particular prescription for a particular insurance subscriber. At the time the authorization number is issued, the third party payor also determines the amount of reimbursement the subscriber will be due for that particular prescription. Therefore, at the time the authorization number is issued, the third party payor database 34 contains not only the subscriber's contract number and the associated payment system access card number, but also the claim authorization number, the authorization number issue date, the amount to be charged for the prescription, and the amount to be reimbursed to the subscriber should a claim be filed. Furthermore, the pharmacy updates its own database with the authorization number and amount to be charged for that particular prescription at the time the authorization number is received. Typically, the required communication between the pharmacy and insurance company to request and receive the claim authorization number is over the Internet, but may include a phone call if there are issues to be resolved.

As illustrated in the preferred embodiment of the invention in FIGS. 1 & 3, each provider 8 has a bar code printer 24 that prints a bar code label 26 that incorporates the claim authorization number as part of the prescription bar code label 26. The bar code scanner 28 scans the bar code label 26 and the information is captured by the provider's point of service terminal 30 in a conventional manner. This information is used as purchase transaction input data. The subscriber's payment system access card is then swiped or the card number is entered in the provider's point of service terminal 30. The provider's point of service terminal 30 includes an Internet connection 10 to a node containing an Internet bank 11 which is to process the credit card transaction via a credit card network 12. The full amount of the purchase is charged to the subscriber's payment system access card in the conventional manner. In addition to being connected to a node containing an Internet bank 11, the provider's point of service terminal 30 also includes an Internet connection 10 to a relational claim records database 16. The information captured by the provider's point of service terminal 30 when the bar code label 26 was scanned by the scanner 28 is transmitted via the Internet connection 10 to the claim records database 16. The claim records database stores pertinent claim information such as the prescription or Rx#, the date filled or purchased, the amount charged, the payment system access card number, and the claim authorization number.

As illustrated in FIGS. 1 & 3, the claim records database 16 is also accessible to the third party payor 18 through an Internet connection 10. The third party payor 18 accesses the claim records database 16 and validates the claim records contained therein. For example, the claim authorization number is located in the third party payor database 34 along with the other pertinent claim information. It is confirmed that there has not been a prior claim paid for this authorization number. The payment system access card number is verified as being associated with the subscriber's contract number for which the authorization number was issued. The date of the sales transaction is confirmed to be within a specified number of days after the authorization number issue date. The amount charged for the prescription is compared with the amount determined by prior agreement and validated.

The third party payor 18 has an Internet connection 10 to the node containing the Internet bank 11, which is to process credit card transactions such as crediting the cardholder credit card account 14 via the credit card network 12 in the conventional manner. The Internet bank 11 is also capable of processing electronic funds transfers such as crediting the cardholder bank account 22 via the automated clearinghouse banking network 20 should the subscriber prefer that method of reimbursement. Assuming that claim records are validated, the third party payor 18 through an Internet connection 10 to the node containing the Internet bank 11 credits the cardholder credit card account 14 or bank account 22 or issues an order for a check to be written to the cardholder for the applicable reimbursement amount. As noted above, the applicable reimbursement amount for a particular prescription is determined when the authorization number is issued to the pharmacy or provider 8. Therefore, the applicable reimbursement amount for the prescription is available virtually instantaneously so that reimbursement may be completely settled during the sales transaction. Even though debiting the cardholder account for the full amount of the purchase and crediting the cardholder account for the applicable reimbursement amount are two separate transactions from two separate sources, printing the reimbursement credit amount as a separate item on a sales receipt is contemplated as being within the scope of the invention.

FIG. 2 illustrates a flow diagram of the use of the automated system for filing a prescription drug claim. Of course, a similar scheme may be used for the filing of other types of claims for reimbursement.

As illustrated in FIG. 2, the first step in the method of the invention is to issue a cobranded healthcare/payment card to the customer or subscriber at step 100. As noted above, the cobranded card is preferably issued through the subscriber's employer in place of the subscriber's conventional healthcare ID card. If the subscriber (employee) is not creditworthy, the employer may issue a securitized card that may or may not be cobranded, thereby exempting the employee from participation in the automated claim filing system described herein. The cobranded card also may be used as a conventional payment card as well as a mechanism for automatically filing a prescription drug claim.

At step 102, the subscriber, cobranded payment card in hand, purchases a prescription drug for which an authorization number has been issued. The entire payment amount is charged to the customer's payment card account in a conventional manner.

At step 104, as illustrated in FIG. 3, the point of service terminal 30 electronically captures pertinent claim information and uses the information to update a claim records database 16. This claim records database 16 stores pertinent claim information such as the prescription or Rx#, the date filled or purchased, the amount charged, the payment system access card number, and the claim authorization number.

At step 106 the third party payor 18 accesses the claim records database 16 and validates the claim records contained therein. For example, the claim authorization number is located in the third party payor database 34 and it is confirmed that there has not been a prior claim paid for this authorization number. The payment system access card number is verified as being associated with the subscriber's contract number for which the authorization number was issued. The date of the sales transaction is confirmed to be within a specified number of days after an authorization number issue date. The amount charged for the prescription is compared with the prior agreement amount associated with the authorization number for the prescription and validated.

At step 108, assuming the claim records are validated in step 106, the third party payor 18 through an Internet connection 10 to the node containing the Internet bank 11 credits the cardholder credit card account 14 or bank account 22 or issues an order for a check to be written to the cardholder for the applicable reimbursement amount. As noted above in the description of FIG. 1, at the time the claim authorization number is issued, the insurance company or third party payor 18 updates its database 34 with information such as the claim authorization number, the amount to be charged for the prescription, and the amount to be reimbursed to the subscriber should a claim be filed. Therefore, the applicable reimbursement amount for the prescription is available virtually instantaneously so that reimbursement may be completely settled during the sales transaction. Printing the reimbursement credit amount as a separate item on the sales receipt is contemplated as being within the scope of the invention.

A preferred embodiment of the invention using bar code will now be described in detail with reference to FIG. 3. As illustrated in FIG. 1, the system 6 of the invention is accessed by a plurality of product/service providers 8. As illustrated in FIG. 3, the preferred embodiment, each such provider 8 has a bar code label printer 24 capable of printing bar code labels 26 that incorporate the claim authorization number as part of the label 26. The bar code scanner 28 is connected to the provider's point of service terminal 30 in a conventional manner. The provider's point of service terminal 30 includes an Internet connection 10 to a node containing a relational claim records database 16.

Operation of this preferred embodiment of the invention is explained in the description of FIG. 1 above.

An additional embodiment of the invention using a provider's existing database will now be described in detail with reference to FIG. 3. As noted above, the pharmacy/healthcare provider 8 maintains a database containing detailed prescription purchase information for their customers. A customer can sign a release form and the pharmacist can print out a list of the customer's prescriptions for up to the last seven years in some instances. This list and therefore the database from which the list is printed contain the pertinent claim information needed for completing a prescription drug claim form. In this additional embodiment of the invention, the pertinent claim information is stored in the pharmacy database 32. FIG. 3 illustrates using the service provider's point of service terminal 30, which includes a monitor, to select a prescription from the pharmacy database 32. Since the pharmacy database 32 is updated when the third party payor issues the claim authorization number, the pharmacy database 32 contains the claim authorization number and the amount to be charged for the prescription being selected. The point of service terminal 30 captures the payment system access card number when the card is swiped or the card number is entered. The amount to be charged for the prescription, the authorization number, and other information is captured from the pharmacy database 32 and this information is used as purchase transaction input data and as input data for updating the claim records database 16. The full amount of the purchase is charged to the subscriber's payment system access card in the conventional manner. The provider's point of service terminal 30 includes an Internet connection 10 to a claim records database 16. The information captured by the provider's point of service terminal 30 during the sales transaction is transmitted via the Internet connection 10 to the claim records database 16.

The remaining operation of this additional embodiment of the invention is the same as explained in the description of FIG. 1 above.

An alternative embodiment of the invention using the third party payor's existing database will now be described in detail with reference to FIGS. 1 & 3. As noted above in the description of FIG. 1, the insurance company or third party payor 18 maintains a third party payor database 34 containing subscriber information and prescription records which include a claim authorization number, an amount to be charged for the prescription, and an amount to be reimbursed to the customer or subscriber should a claim be filed. The provider's point of service terminal 30 captures the payment system access card number when the card is swiped or when the card number is entered. Also, the provider's point of service terminal 30 accesses the third party payor's database 34 through an Internet connection 10. Swiping the payment system access card causes the system to display prescriptions in the third party payor's database 34 for this particular subscriber. These prescriptions are displayed on the monitor connected to the service provider's point of service terminal 30.

Prescriptions to be purchased are selected and this information is captured from the third party payor's database 34 and is used as purchase transaction input data for the sales transaction. The provider's point of service terminal 30 includes an Internet connection 10 to a node containing an Internet bank 11 which is to process the credit card transaction via a credit card network 12. The full amount of the purchase is charged to the subscriber's payment system access card in the conventional manner. The third party payor's database 34 is updated to show the prescriptions have been purchased. The updated third party payor's database 34 then, in effect, becomes the claim records database 16 and is of course accessible to the third party payor. The applicable reimbursement amount is accessed and the third party payor 18 through an Internet connection 10 to the node containing the Internet bank 11 credits the cardholder credit card account 14 or bank account 22 or issues an order for a check to be written to the cardholder for the applicable reimbursement amount.

Those skilled in the art will appreciate that the automated system of the invention eliminates the tedious effort required by customers or insurance subscribers to collect the pertinent prescription claim information, to complete and mail prescription drug claim forms, and to track which prescription claims have been filed and which have not. Furthermore, the invention dramatically reduces expenses associated with paying employees for opening prescription drug claim mail, microfilming, keying, and processing paper generated prescription drug claims. This is a substantial improvement over the present system of manually filing and processing paper claim forms.

It will be appreciated by those skilled in the art that even though numerous characteristics and advantages of the present invention have been set forth in the foregoing description, together with details of the structure and function of the invention, the disclosure is illustrative only and numerous alternate embodiments are possible without departing from the novel teachings of the invention. For example, the pharmacy database 32, which already contains the authorization number, could be updated by the point of service terminal 30 with a payment system access card number, an amount charged to the cardholder credit card account for the prescription, and a sales transaction date. The pharmacy database 32 could then, in effect, become the claim records database 16 and be accessed by the third party payor 18 through an Internet connection 10. Also, the information captured by the point of service terminal 30 could in turn be captured by a smart card during the sales transaction. The smart card could then be used to update the claim records database 16 or the smart card could be made available to the third party payor directly via an Internet connection and thus become the claim records database 16. Alternatives to the bar code label include a magnetic stripe, a chip, or even keying in the claim authorization number. These and other modifications may be made in detail within the principles of the invention to the full extent indicated by the broad general meaning of the terms in which the appended claims are expressed.

I claim:

1. A method of filing a prescription claim within a health insurance indemnity system, wherein an insurance subscriber files a prescription claim by using a payment card in a purchase transaction for a prescription, the method comprising:

issuing said payment card having a payment card number to said insurance subscriber;

linking said payment card number to an insurance contract number for said insurance subscriber within a database of an insurance company or third party payor covering said insurance subscriber;

said insurance company or third party payor issuing a claim authorization or approval number for said prescription for said insurance subscriber to a specific provider prior to conducting said purchase transaction for said prescription;

said insurance subscriber using said payment card to pay in full for said prescription as part of said purchase transaction;

incorporating said claim authorization or approval number and other pertinent claim information as part of purchase transaction input data for said prescription;

providing a point of service terminal for electronically capturing said purchase transaction input data for said prescription;

wherein said purchase transaction input data resides in a data storage device; wherein the data storage device comprises a bar code label;

said point of service terminal having a computer connection to a claim records database for updating said claim records database with said pertinent claim information thereby causing an updated claim records database; wherein said pertinent claim information includes at least said claim authorization or approval number;

said insurance company or third party payor accessing said updated claim records database through an Internet or other computer connection and validating said pertinent claim information contained therein;

said insurance company or third party payor accepting said updated claim records database as a claim for reimbursement from said insurance subscriber for said prescription upon validating said pertinent claim information contained in said updated claim records database.

2. The method of claim 1 wherein said prescription comprises prescription drugs, prescription healthcare equipment, prescribed treatments, or combinations thereof.

3. The method of claim 1 wherein said specific provider is selected from the group consisting of a drug manufacturer, a healthcare equipment manufacturer, a drug distributor, a healthcare distributor, a physician, and combinations thereof.

4. The method of claim 1 wherein said purchase transaction input data resides in a data storage device selected from the group consisting of a magnetic stripe, a chip, a provider database, a third party payor database, and combinations thereof.

5. The method of claim 1 wherein said claim records database is said service provider's claim records database.

6. The method of claim 1 wherein said claim records database is said insurance company's or third party payor's claim records database.

7. The method of claim 1 wherein said point of service terminal accesses said claim records database using an Internet connection to a node containing said claim records database.

8. The method of claim 1 wherein said claim records database is a database that resides on a computer of said specific provider.

9. The method of claim 1 wherein said claim records database is a database that resides on a computer of said insurance company or third party payor.

* * * * *